(12) United States Patent
Newton et al.

(10) Patent No.: US 9,629,339 B2
(45) Date of Patent: Apr. 25, 2017

(54) SYSTEMS AND METHODS FOR REARING INSECT LARVAE

(75) Inventors: G. Larry Newton, Tifton, GA (US); D. Craig Sheppard, Tifton, GA (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 747 days.

(21) Appl. No.: 13/992,170

(22) PCT Filed: Feb. 21, 2012

(86) PCT No.: PCT/US2012/025931
§ 371 (c)(1),
(2), (4) Date: Jun. 6, 2013

(87) PCT Pub. No.: WO2012/115959
PCT Pub. Date: Aug. 30, 2012

(65) Prior Publication Data
US 2013/0319334 A1     Dec. 5, 2013

Related U.S. Application Data

(60) Provisional application No. 61/444,870, filed on Feb. 21, 2011.

(51) Int. Cl.
   *A01K 29/00*     (2006.01)
   *A01K 5/00*      (2006.01)
   *A01K 67/033*    (2006.01)

(52) U.S. Cl.
   CPC .............. *A01K 29/00* (2013.01); *A01K 5/00* (2013.01); *A01K 67/033* (2013.01)

(58) Field of Classification Search
   CPC ........ A01K 29/00; A01K 5/00; A01K 67/033; A01K 67/0331; A01K 67/0332;
(Continued)

(56) References Cited

U.S. PATENT DOCUMENTS 3,339,530 A * 9/1967 Gillette .................. A01K 5/00
                                                                         119/51.11
3,353,654 A * 11/1967 Ferris ....................... A01K 5/00
                                                                         198/670
(Continued)

FOREIGN PATENT DOCUMENTS

FR     2387596 A1 * 11/1978 ......... A01K 67/0331
FR     2475358 A1 *  8/1981 ......... A01K 67/0331
(Continued)

OTHER PUBLICATIONS

The International Preliminary Report on Patentability dated Aug. 29, 2013.
(Continued)

*Primary Examiner* — Stanton L Krycinski
(74) *Attorney, Agent, or Firm* — Thomas | Horstemeyer, LLP

(57) ABSTRACT

In one embodiment, a system for rearing larvae includes a plurality of culture trays arranged in at least one stack of trays, each stack comprising multiple levels of trays, each tray comprising an open-topped basin adapted to receive larvae and larval food, a feed delivery system adapted to automatically deliver larval feed to individually selected culture trays, and a water delivery system adapted to automatically deliver water to the culture trays.

30 Claims, 14 Drawing Sheets

(58) Field of Classification Search
CPC ............ A01K 67/0333; A01K 67/0334; A01K 67/0335; A01K 67/0336; A01K 67/0337; A01K 67/0338; A01K 67/0339
See application file for complete search history.

(56) References Cited

U.S. PATENT DOCUMENTS

| | | | | |
|---|---|---|---|---|
| 3,561,403 | A * | 2/1971 | Wilson, Jr. ........... | A01K 5/0216 119/51.11 |
| 4,850,305 | A * | 7/1989 | Georgi ................. | A01K 67/033 119/303 |
| 5,178,094 | A * | 1/1993 | Carr ....................... | A01K 67/04 119/6.5 |
| 5,819,685 | A | 10/1998 | Kappelt et al. | |
| 6,474,259 | B1 * | 11/2002 | Gaugler ............... | A01K 67/033 119/6.7 |
| 8,951,787 | B1 * | 2/2015 | O'Donnell .......... | C05F 17/0009 435/290.1 |
| 2003/0143728 | A1 | 7/2003 | Paul | |
| 2011/0139075 | A1 * | 6/2011 | Shapiro Ilan ........ | A01K 67/033 119/6.5 |

FOREIGN PATENT DOCUMENTS

| | | | | |
|---|---|---|---|---|
| FR | 2609597 | A1 * | 7/1988 | ......... A01K 67/0331 |
| JP | WO 2012073948 | A1 * | 6/2012 | ........... A01K 67/033 |
| JP | WO 2012073949 | A1 * | 6/2012 | ........... A01K 67/033 |
| KR | 200414744 | Y1 | 4/2006 | |
| KR | 100654253 | B1 | 12/2006 | |
| KR | 100689671 | B1 | 2/2007 | |

OTHER PUBLICATIONS

The International Search Report and Written Opinion dated Sep. 25, 2012.

* cited by examiner

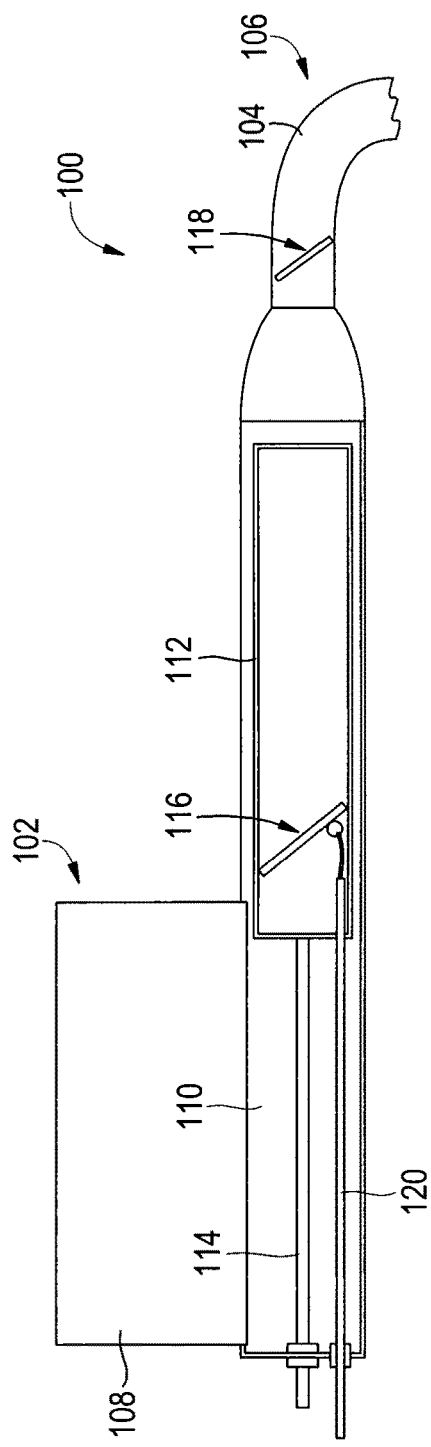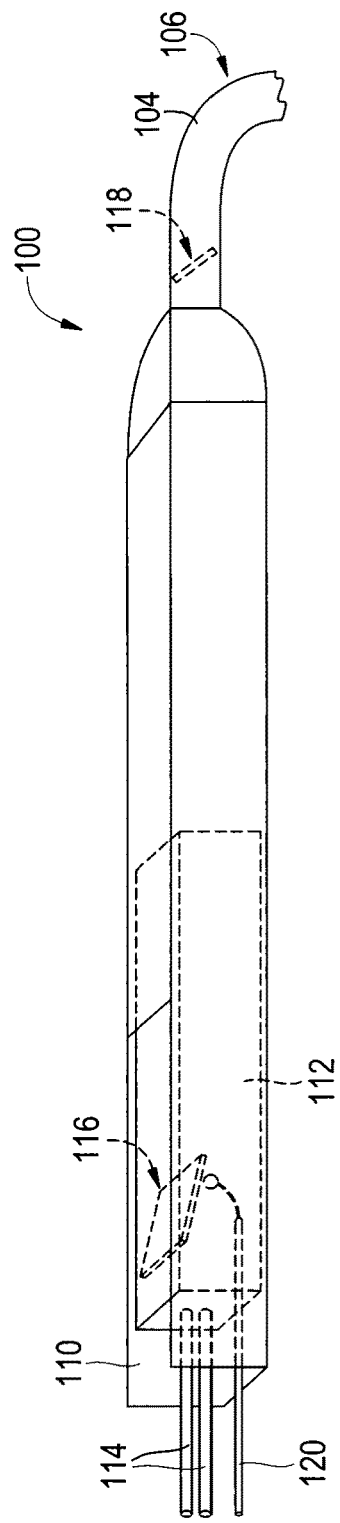
FIG. 8A
FIG. 8B

SYSTEMS AND METHODS FOR REARING INSECT LARVAE

CROSS REFERENCE TO RELATED APPLICATION

This application is the 35 U.S.C. §371 national stage of PCT application having serial number PCT/US2012/025931, filed on Feb. 21, 2012. This application also claims priority to and benefit of U.S. Provisional Application No. 61/444,870 filed on Feb. 21, 2011, both of which are incorporated by reference in their entireties.

STATEMENT REGARDING FEDERALLY SPONSORED RESEARCH OR DEVELOPMENT

This invention was made with government support under grant number LAK-2006-00598 awarded by the United States Department of Agriculture. The Government has certain rights in the invention.

BACKGROUND

There have been many proposals for, and attempts at, utilizing insects to process waste materials, especially animal manures, into valuable products. For the most part, these schemes have not worked well, or the level of productivity has not been great enough to support the process, typically due to operating and labor costs. Most often, these are batch processes that have included loading a culture vessel with a large quantity of larval feed (manure or other wastes), adding an appropriate number of insect eggs or first-stage larvae, allowing time for the larvae to consume the feed, followed by harvest of the mature larvae or pupae. Unfortunately, such systems provide less than optimum nutrition for the larvae because, during the days or weeks that the larvae are in the culture, the feed is also undergoing microbial decomposition and spoilage, thus reducing the conversion efficiency of the larvae. If this problem is avoided by daily feeding, the labor requirement severely limits the scope of an operation.

Continuous culture systems have also been proposed, especially for flies that have migrating larvae, for example the black soldier fly, whose larvae leave the feeding location before pupation. Such systems have been proposed for use under animals housed on slatted floors or in wire cages, and for small systems used to treat small-scale food processing waste streams and restaurant waste. In all these cases, the larvae are usually fed at least once per day, overcoming the limitations of adding several weeks of larval feed at the same time that small larvae are added. However, there is often difficulty in matching larvae numbers and larval feed supply and achieving optimum self-harvest. If the population is in significant excess of the larval feed supply, immature larvae may leave the culture tray or basin, thus missing their most rapid growth and greatest larval feed consumption period. If the larval population is significantly below the larval feed supply, some areas of the culture tray will be unoccupied by feeding larvae, thus providing a location for migrating larvae to undergo pupation without actually leaving the culture tray or basin and leading to production of at least some flying adults.

From the foregoing discussion it can be appreciated that it would be desirable to have an improved system and method for rearing larvae that overcomes one or more of the disadvantages described above.

BRIEF DESCRIPTION OF THE DRAWINGS

The present disclosure may be better understood with reference to the following figures. Matching reference numerals designate corresponding parts throughout the figures, which are not necessarily drawn to scale.

FIGS. 8A and 8B are side views of a further embodiment of a feed delivery system.

DETAILED DESCRIPTION

As described above, it would be desirable to have an improved system and method for rearing larvae. Disclosed herein are systems and methods for raising larvae, and particularly insect larvae such as fly larvae, that can then be used as animal feed or processed for use as other commodities. The systems and methods employ a multiplicity of stacked larvae culture trays that can occupy most of the air space of a building to increase larvae production. In some embodiments, the systems and methods provide for automated mechanical feeding and watering that enable the larvae to be fed and watered at frequent intervals with little manual labor. Accordingly, the systems and methods overcome current impediments to large-scale larvae production.

In some embodiments, the larvae are reared in a continuous culture scheme. In such a scheme, the culture trays have built-in larvae exits that enable mature larvae to migrate out of the culture and be transported to a centralized collection location. Young larvae can be added every few days and self-harvesting occurs on a continual basis as the mature larvae exit the trays. Once residue accumulates to near the larvae exits (e.g., after several months), the tray can be emptied and the process can be repeated.

In other embodiments, the larvae are reared in a batch culture scheme. In such a scheme, the culture trays have no larvae exits. The number of young larvae that the tray can support after those larvae reach maturity is initially added to the tray, and the feeding rate is increased as the larvae mature. Once the larvae reach the desired stage of maturity (e.g., after 10-20 days), the entire contents of the trays are removed and the larvae are harvested from the other material by using appropriate separating methods. The next batch of larvae can then be added to the trays and the process repeated.

Regardless of the particular rearing scheme that is employed, the trays can be arranged in a way that enables a single feed delivery system and a single water delivery system to supply all of the trays. The room or building in which the rearing system is housed can include ventilation to remove moisture, especially during colder seasons, and excess heat during the summer. In some embodiments, the ventilation system includes one or more heat exchangers so that heating costs during colder seasons can be reduced.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
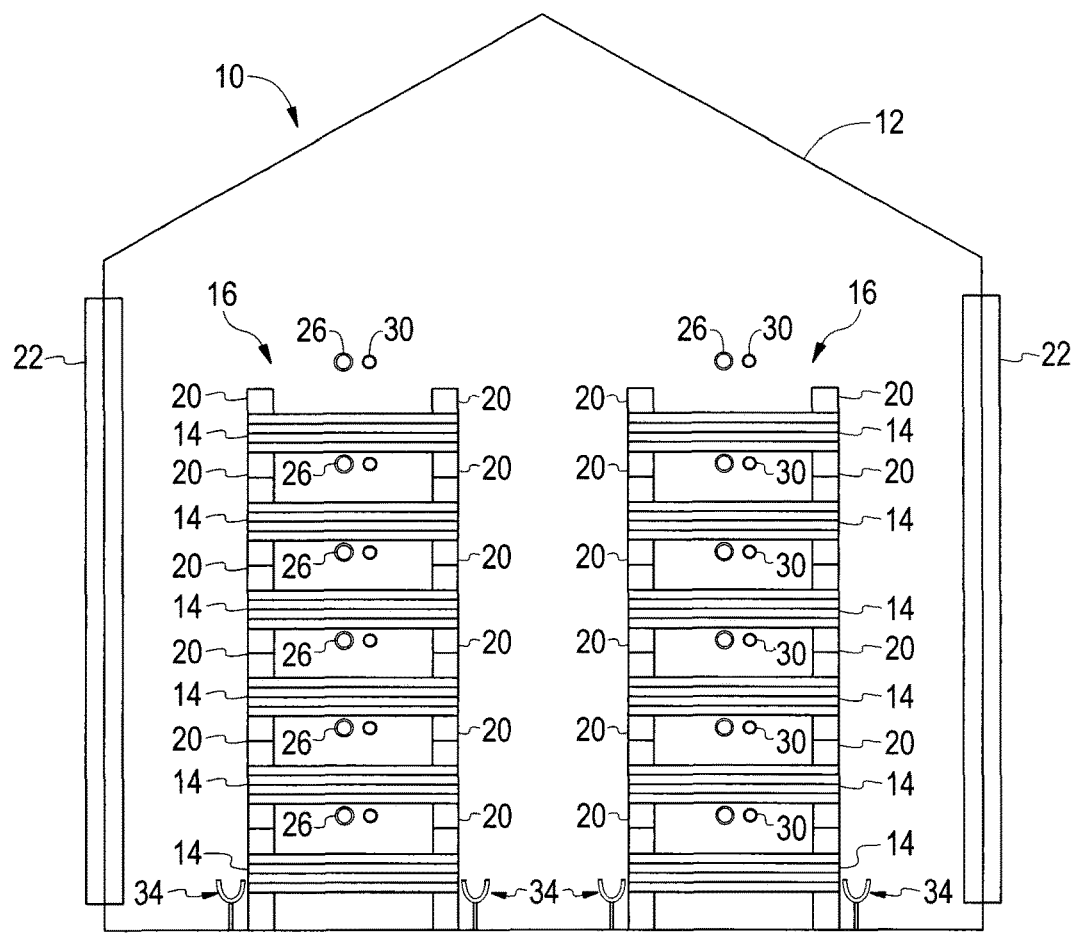
FIG. 1 is an end view of a first embodiment of a larvae rearing system.
Figure 2:
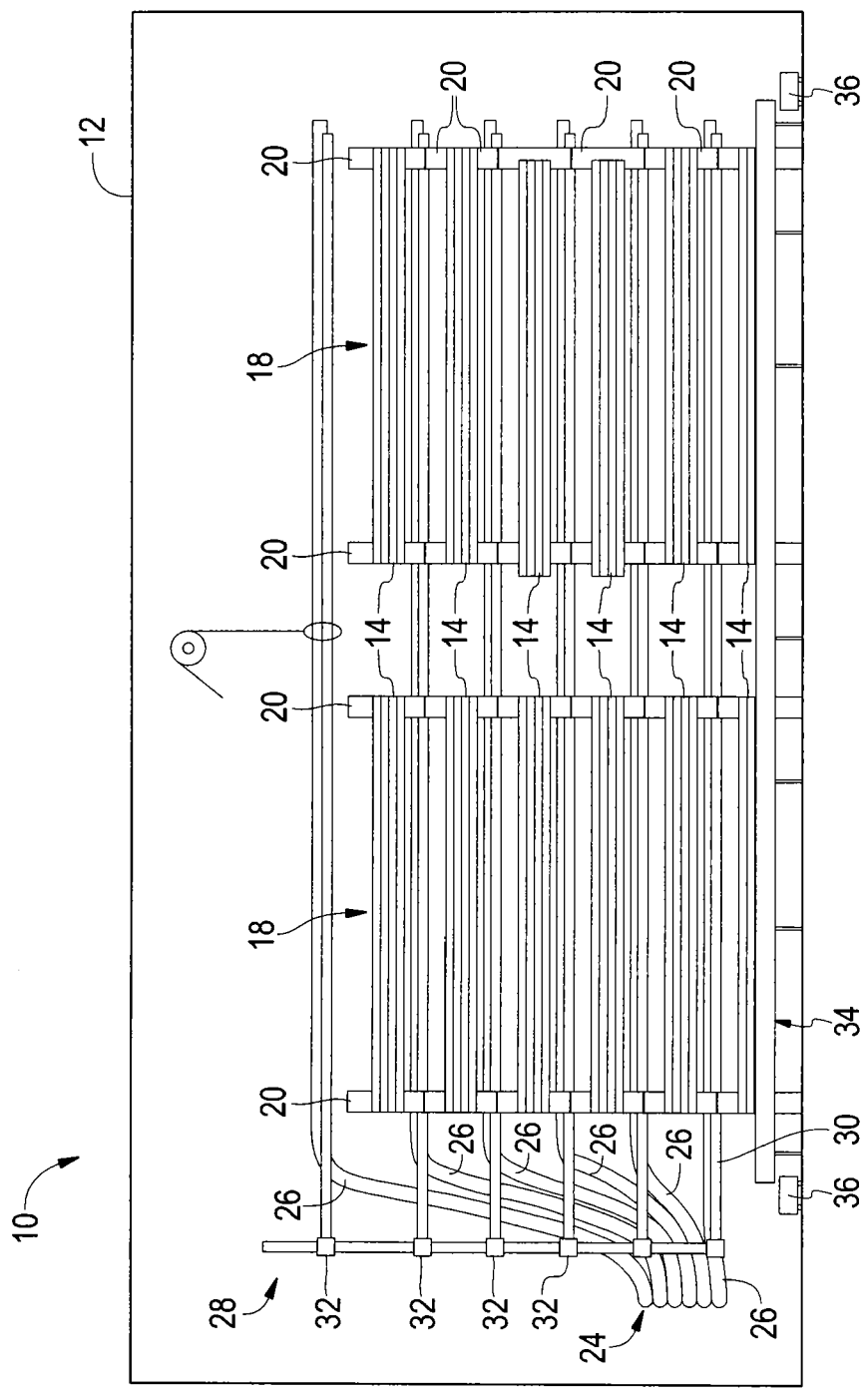
FIG. 2 is a side view of the larvae rearing system of FIG. 1.

FIGS. 1 and 2 illustrate a first embodiment of an insect larvae rearing system 10, which is housed within a building 12. As is described below, the system 10 is well suited for a continuous culture scheme. The system 10 includes a plurality of vertically stacked culture trays 14 that are contained in longitudinal rows 16 (FIG. 1) that extend along the length of the building 12. In the example shown in the figures, there are two such rows 16, and each row contains two different groups 18 (FIG. 2) of stacked trays 14. Each group 18 includes six trays so that the system 10 includes a total 24 trays. Of course, greater or fewer rows, groups, and trays can be used, depending upon the desired number of larvae that are to be reared. In large-scale systems, thousands of trays 14 can be used.

Each culture tray 14 forms an open-topped basin in which larvae and larval feed (e.g., organic waste such as manure, restaurant waste, and brewer's grains) can be provided. In the embodiment of FIGS. 1 and 2, trays 14 are generally rectangular and each has a leg 20 provided at each of its four corners. Each leg 20 is adapted to couple with at least one leg of another tray in the stack. More specifically, the bottom of each leg 20 is adapted to couple to the top of a leg of a lower tray 14 in the stack, and the top of each leg is adapted to couple to the bottom of a leg of an upper tray in the stack. With such functionality, the legs 20 form a framework that supports the trays 14 and that can be used to build stacks of trays of nearly any desired height. In addition, the stacks can be broken down as necessary for cleaning of the trays 14. Specific tray embodiments that can be used in the system 10 are illustrated in FIGS. 13-23, which are discussed in detail below.

With specific reference to FIG. 1, the walls of the building 12 in which the larvae rearing system 10 is housed can support heat exchangers 22 that recapture heat that may otherwise be lost when venting out of the building to reduce humidity. For example, warm, moist air from within the building 12 can be vented to the atmosphere and the heat that it contains can be transferred by the heat exchangers 22 to the dry air that is brought into the building.

With specific reference to FIG. 2, the larvae rearing system 10 further includes a feed delivery system 24 (only part of the system visible in the figure) that comprises a plurality of feed lines 26 that linearly extend along each level of each row 16 of trays. Accordingly, in the example embodiment of FIGS. 1 and 2, there are six feed lines 26 for each row 16 of trays, one for each level of the stacks. With further reference to FIG. 2, the system 10 also includes a water delivery system 28 (only part of the system visible in the figure) that comprises a plurality of water lines 30 that also linearly extend along each level of each row 16 of trays. In some embodiments, the flow of water to each of the water lines 30 is controlled with electronically-controlled (e.g., solenoid) valves 32, and the water is delivered to each tray 14 through nozzles (not shown) provided along the lengths of the lines. With this configuration of the feed delivery system 24 and the water delivery system 28, there is a feed line 26 and a water line 30 positioned above each tray 14, as is depicted in FIG. 1. In some embodiments, the feed and water lines 26, 30 can be supported by cables from the ceiling of the building 12 and can be raised out of the way when the stacks are to be broken down.

With continued reference to FIGS. 1 and 2, the larvae rearing system 10 further comprises larvae collection gutters 34. As is shown in the figures, the gutters 34 are positioned on or near the floor at the base of each stack of trays 14 so that mature larvae that migrate from the trays 14 are caught and collected by the gutters. In some embodiments, as when the system 10 is a large-scale system, the gutters 34 can comprise integral conveyors that are used to deliver the larvae to the ends of the rows 16. As is shown in FIG. 2, a further conveyor 36 can be provided at one or each end of the rows 16 to convey the collected larvae to a separate processing station (not shown).

Figure 3:
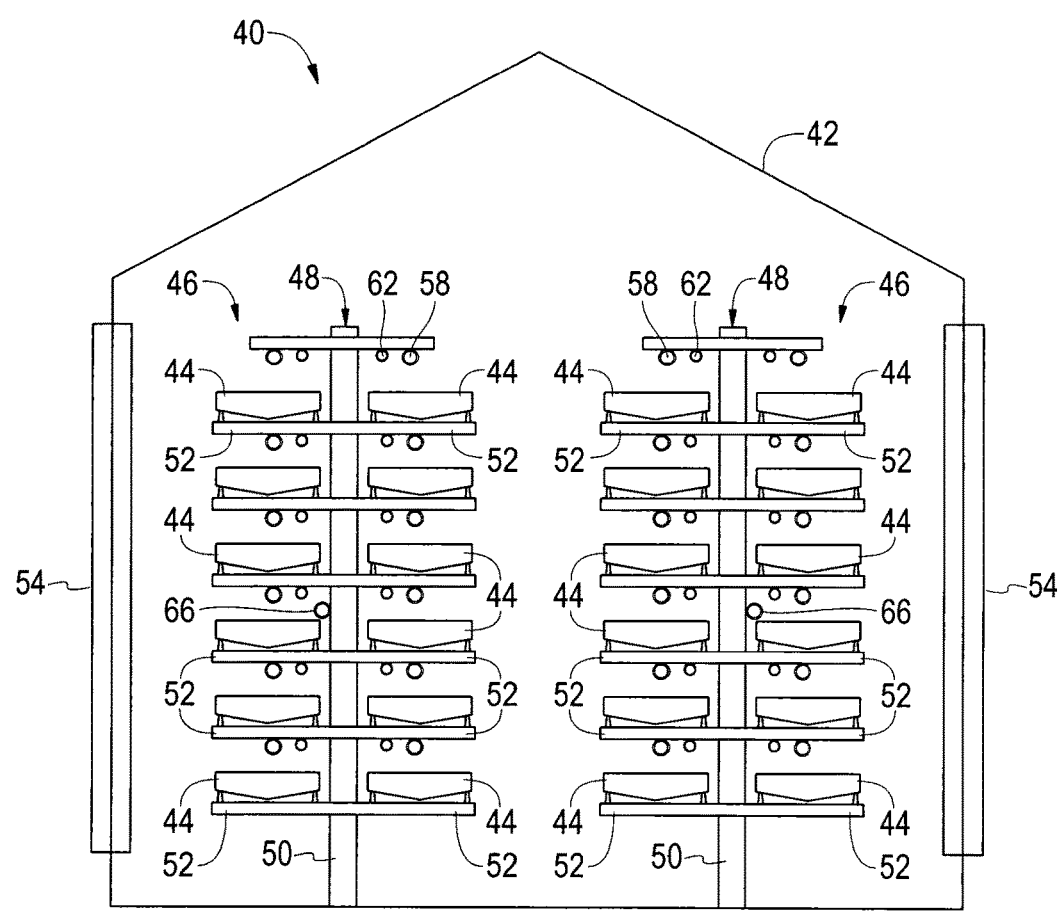
FIG. 3 is an end view of a second embodiment of a larvae rearing system.
Figure 4:
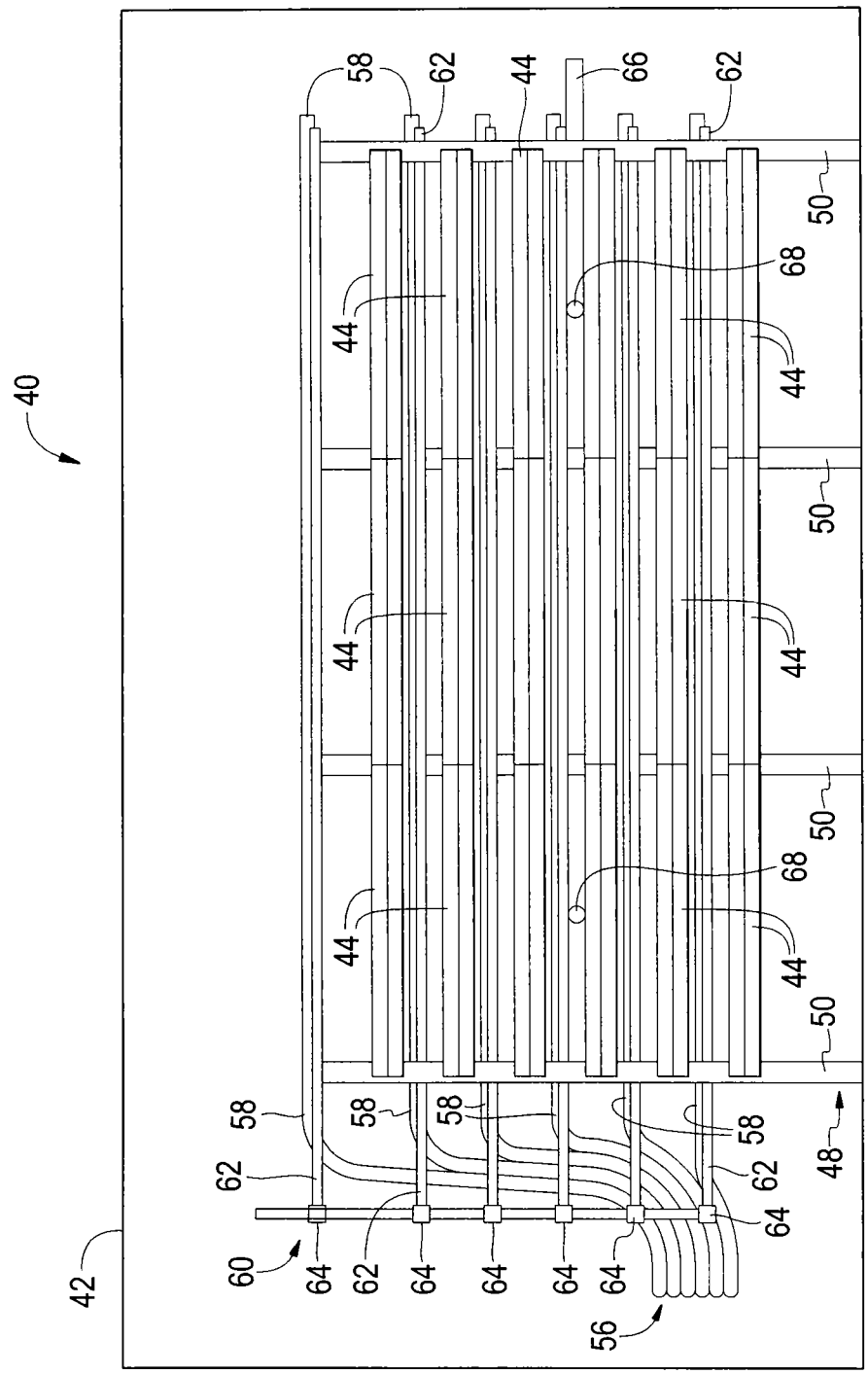
FIG. 4 is a side view of the larvae rearing system of FIG. 3.

FIGS. 3 and 4 illustrate a second embodiment of an insect larvae rearing system 40, which is housed within a building 42. As is described below, the system 40 is well suited for a batch culture scheme. The system 40 includes a plurality of vertically stacked culture trays 44 that are contained in longitudinal rows 46 (FIG. 3) that extend along the length of the building 42. In the example shown in the figures, there are two such rows 46 and each includes 36 trays so that the system 40 includes a total 72 trays. Of course, greater or fewer rows and trays can be used, depending upon the desired number of larvae that are to be reared. In large-scale systems, thousands of trays 44 can be used.

Each culture tray 44 forms an open-topped basin in which larvae and larval feed (e.g., organic waste such as manure, restaurant waste, and brewer's grains) can be provided. In the embodiment of FIGS. 3 and 4, trays 44 are generally rectangular but each has a sloped bottom having a generally V-shaped cross-section. Unlike the trays 14, the trays 44 do not include integrated legs that form a framework that supports the trays. Instead, each tray 44 is supported by an independent frame 48 that includes multiple support posts 50 from which laterally extend support platforms 52. The support platforms 52 support the trays 44 in a cantilevered orientation so that there is easy access to the tops of the trays, which facilitates harvesting and cleaning of the trays 44. Specific tray embodiments that can be used in the system 40 are illustrated in FIGS. 25-33, which are discussed in detail below. In some embodiments, the trays 44 can be supported by an A-frame structure (not shown) in which the trays of lower levels are separated by a greater distance than trays of higher levels. A-frame structures are less expensive to construct than a support system based on vertical posts. Such structures also provide easier access to the trays with a vacuum pipe (described below) that is used to remove the contents of the trays during harvesting.

With specific reference to FIG. 3, the walls of the building 42 in which the larvae rearing system 40 is housed can support heat exchangers 54 that recapture heat that may otherwise be lost when venting air within the building to reduce humidity. For example, warm, moist air from within the building 42 can be vented to the atmosphere and the heat that it contains can be transferred by the heat exchangers 54 into the dry air that is brought into the building.

With specific reference to FIG. 4, the larvae rearing system 40 further includes a feed delivery system 56 (only part of the system visible in the figure) that comprises a plurality of feed lines 58 that linearly extend along each level of each row 46 of trays 44. Accordingly, in the example embodiment of FIGS. 3 and 4, there are six feed lines 58 for each row 46 of trays, one for each level of the stacks. With further reference to FIG. 4, the system 40 also includes a water delivery system 60 (only part of the system visible in the figure) that comprises a plurality of water lines 62 that also linearly extend along each level of each row 46 of trays. In some embodiments, the flow of water to each of the water lines 62 is controlled with electronically-controlled (e.g., solenoid) valves 64, and the water is delivered to each tray 44 through nozzles (not shown) provided along the lengths of the lines. With this configuration of the feed delivery system 56 and the water delivery system 60, there is a feed line 58 and a water line 62 positioned above each tray 44, as is depicted in FIG. 3. In some embodiments, the feed and water lines 58, 62 can be mounted to the underside of the support platforms 52.

Also illustrated in FIGS. 3 and 4 are vacuum lines 66 that can be used to remove material from within the culture trays 44. As is shown in FIG. 4, the vacuum lines 66 can comprise periodic connection ports 68 to which a flexible vacuum hose (not shown) can be connected. The connection ports 68 can be provided at various positions along the rows 46. For instance, a connection port 68 can be provided every 20 to 30 feet along the lengths of the rows 46 and a 15 to 30 foot vacuum hose can be connected to the ports. The hose can then be used by a worker with a rolling ladder deck to clear the trays 44. Notably, similar vacuum lines can be provided in the system 10 of FIGS. 1 and 2, if desired.

Figure 5:
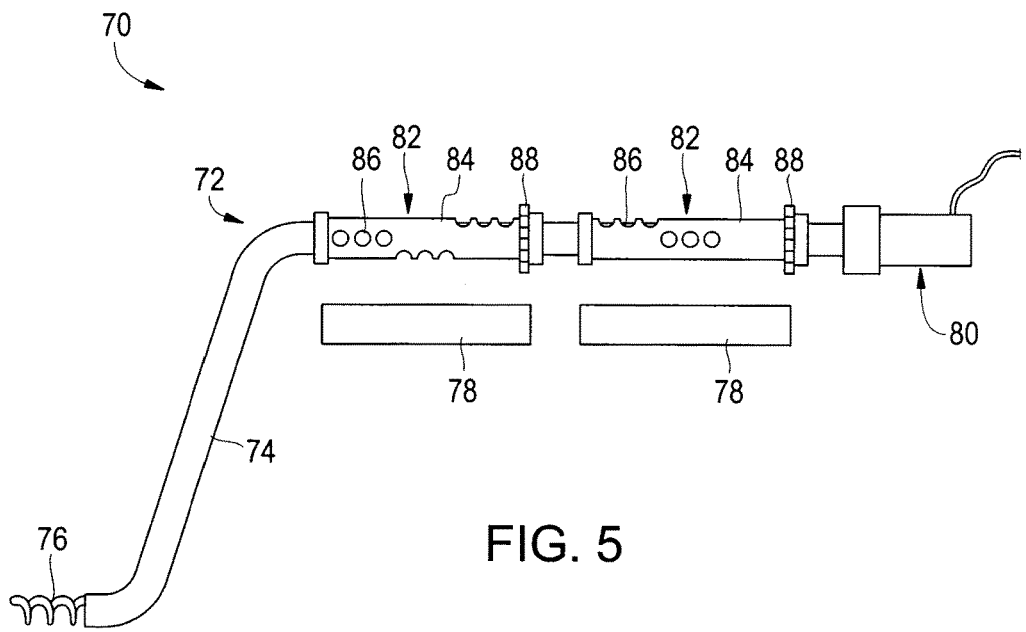
FIG. 5 is a side view of an embodiment of a feed line.
Figure 6:
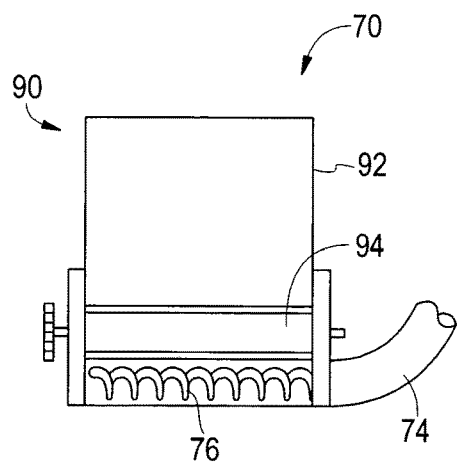
FIG. 6 is a side view of an embodiment of a feed delivery system.
Figure 7:
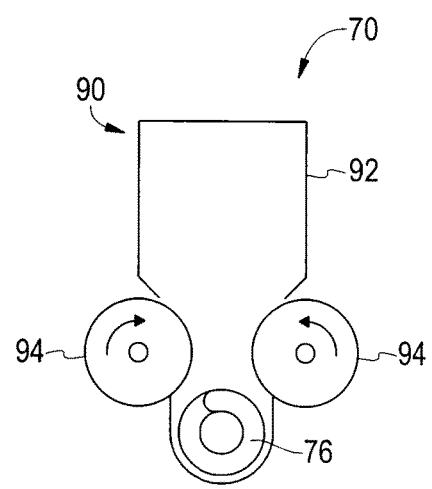
FIG. 7 is an end view of the feed delivery system of FIG. 6.

FIGS. 5-7 together illustrate a first embodiment of a feed delivery system 70 that can be used to supply feed to either the larvae rearing system 10 or larvae rearing system 40. Beginning with FIG. 5, the system 70 includes a feed line 72, which can be used as a feed line 26 (FIGS. 1 and 2) or a feed line 58 (FIGS. 3 and 4). In some embodiments, the feed line 72 comprises a feed tube 74 that houses a flexible, hollow spring-type auger 76. By way of example, the auger 76 can be a Choretime Flexauger™. When it is desired to supply feed to trays 78 of the larvae rearing system, the auger 76 can be rotated within the tube 74 by a motor 80 that is provided at a distal (downstream) end of the feed line 72. Accordingly, the auger 76 and motor 80 together provide a means for driving feed along the feed line 72. Positioned along the feed line 72 are feeding units 82 that can be used to individually supply feed to selected trays 78. In some embodiments, the feeding units 82 each comprise a rotatable sleeve 84 that fits closely over the outside surface of the feed tube 74. Each sleeve 84 is provided with one or more series of holes 86 that can be made to align with similar holes provided in the underside of the feed tube 74 (not shown). By way of example, one or more motors (not shown) can be used drive sprockets 88 associated with each sleeve 82 to individually rotate the sleeves about the feed tube 74 until the holes 86 in the sleeve align with the downwardly-facing holes of the feed tube. With such functionality, the feed delivery system 70 can be used selectively to supply feed to one or more individual trays 78 that are selected to receive feed. In the example of FIG. 5, the first sleeve 84 (on the left) is oriented so as to be able to pass feed carried by the auger 76 to the first tray 78 (also on the left).

FIGS. 6 and 7 illustrate a feed hopper 90 that can be used to supply feed into the feed tube 74 and the auger 76. As is shown in those figures, the hopper 90 includes a compartment 92 into which feed can be dropped, for example through a hinged lid (not shown). The feed contained in the compartment 92 can be driven down into the auger 76 using counter rotating rollers 94.

FIGS. 8A and 8B illustrate a second embodiment of a feed delivery system 100 that can be used to supply feed to either the larvae rearing system 10 or larvae rearing system 40. The system 100 is particularly useful with relatively wet feeds, such as slurries. With reference to FIG. 8A, the system 100 includes hopper 102 that can be used to supply feed to the feed tube 104 of a feed line 106. The hopper 102 includes a compartment 108 into which feed can be dropped or poured, for example through a hinged lid (not shown). The feed contained in the compartment 108 can drop or flow down into a pump cavity 110 where it can be pumped into the feed tube 104 using a hollow piston 112 that is driven by one or more piston rods 114. In some embodiments, the system 100 includes check valves that ensure that the feed is only pumped in the direction of the culture trays when the piston 112 is actuated and prevent feed backflow. In the example embodiment, the system 100 includes a first check valve 116 that is contained within the piston 112 and a second check valve 118 that is positioned at or within the inlet of the feed tube 104. In some embodiments, the first check valve 116 can be actuated using an actuating rod 120. The first check valve 116 is shown closed in FIG. 8A (during the drive stroke) and is shown open in FIG. 8B (during the return stroke).

Figure 9:
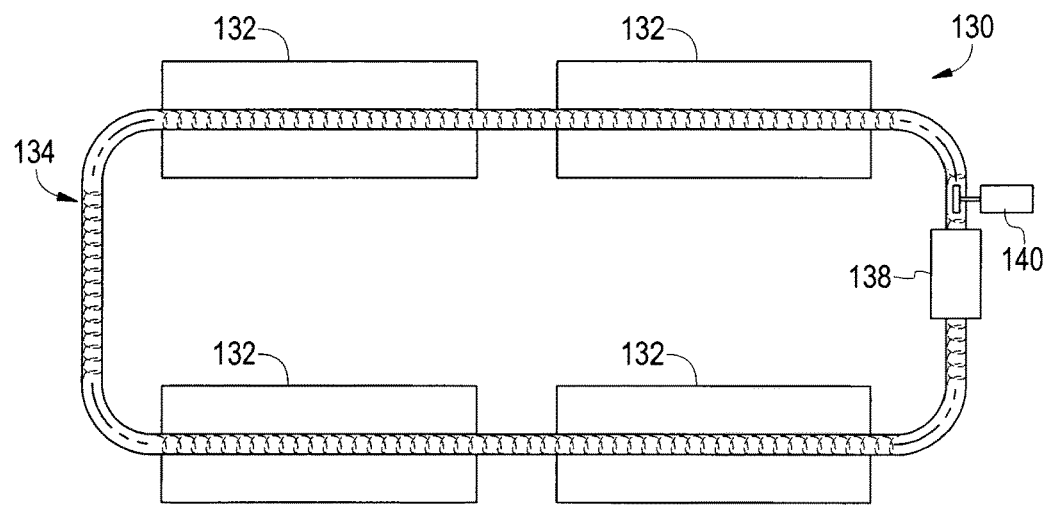
FIG. 9 is a top view of a further embodiment of a feed delivery system.
Figure 10:
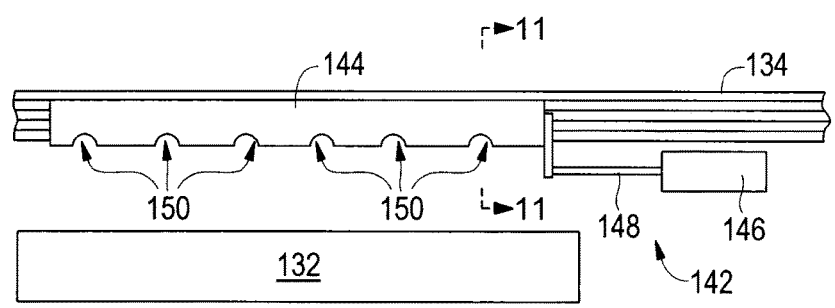
FIG. 10 is a side view of an embodiment of a feeding unit for use in a feed delivery system.
Figure 11:
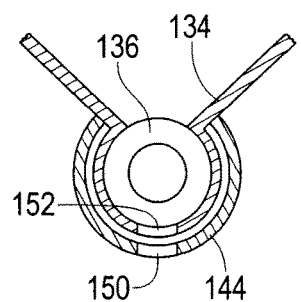
FIG. 11 is a cross-sectional view of a feed delivery tray of a feed delivery system.

FIGS. 9-11 illustrate a third embodiment of a feed delivery system 130 that can be used to supply feed to a larvae rearing system. The system 130 is particularly useful for delivering dry or somewhat wet solids, such as brewer's grains to culture trays 132 of the rearing system. Beginning with FIG. 9, the system 130 comprises feed lines in the form of elongated, open-topped feed delivery trays 134 that are each positioned above the culture trays 132 of a level of trays in the rearing system. Provided within the tray 134 is a drag auger 136 that can be used to drag feed that is deposited in the tray 134 by a hopper 138. The auger 136 can be dragged by a dedicated motor 140.

With reference to FIG. 10, mounted to the feed delivery tray 134 above each culture tray 132 is a feeding unit 142 that can be independently operated to provide feed to the selected culture trays. As is shown in FIG. 10, the feeding unit 142 comprises a slidable sleeve 144 that can be laterally displaced along the length of the feed delivery tray 134 by a linear actuator 146 and its arm 148. In some embodiments, the linear actuator 146 comprises a screw jack. As in the feeding system embodiment of FIG. 5, the sleeve 144 is provided with holes 150. With reference to the cross-section of FIG. 11, the feed delivery tray 134 comprises downwardly-facing holes 152 that are formed on its underside. In a first lateral position of the sleeve, the holes 150 do not align with the holes 152 and no feed will be provided to the culture tray 132. In a second lateral position, however, the holes 150 do align with the holes 152 and feed can drop from the feed delivery tray into the culture tray 132. Through individual control over selected feeding units 142, the feed delivery system 130 can also be used selectively to supply feed to one or more individual trays 132 that are selected to receive feed.

Figure 12A:
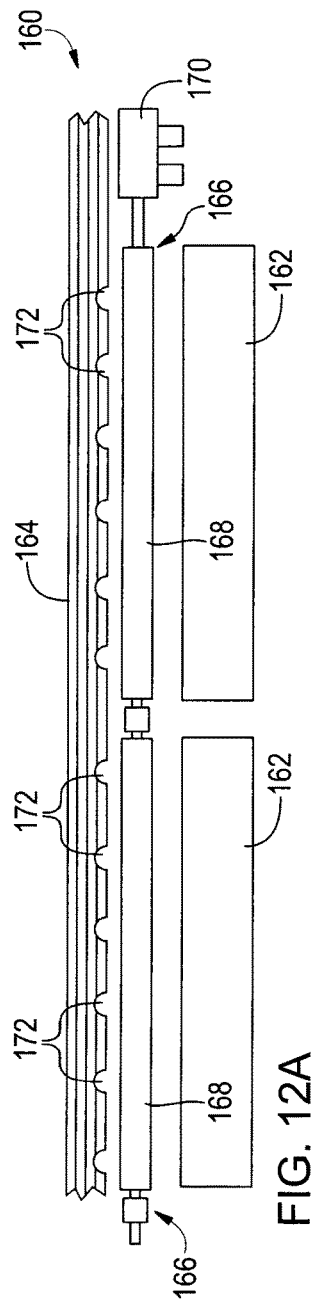
FIGS. 12A-12C are side views of a further embodiment of a feeding unit for use in a feed delivery system.
Figure 12B:
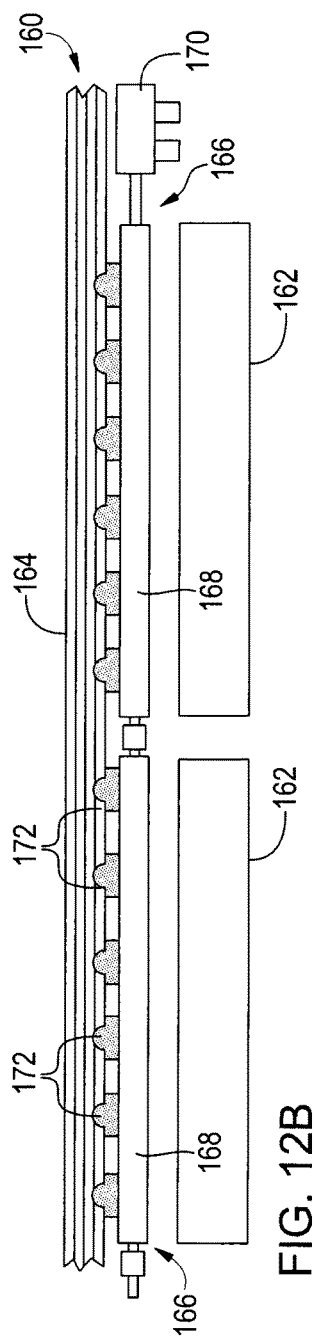
Figure 12C:
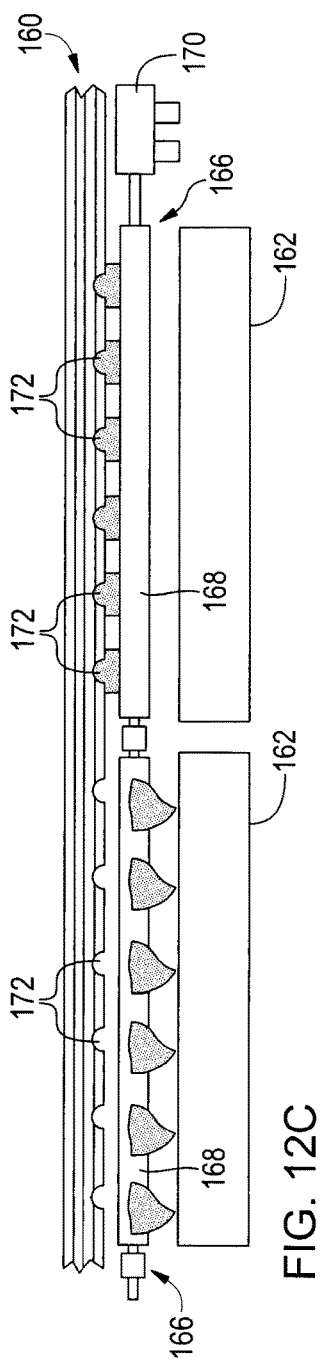

FIGS. 12A-12C illustrate a fourth embodiment of a feed delivery system 160 that can be used to supply feed to a larvae rearing system. The system 160 is also useful for delivering wet or dry solids to culture trays 162 of the rearing system. The system 160 shares some similarities with the system 130 described in relation to FIGS. 9-11. Specifically, the system 160 comprises an elongated, open-topped feed delivery tray 164 that extends above each culture tray 162 of the rearing system and that, for example, contains a drag auger (not shown). Mounted to the feed delivery tray 164 above each culture tray 162 is a feeding unit 166 that can be used to independently provide feed to selected culture trays. In this embodiment, however, the feeding units 166 comprise feed collection trays 168 that can be rotated by a rotational actuator 170 to dump feed into the culture tray 162. In some embodiments, the rotational actuator 146 comprises a gear motor.

As the drag auger is used to drag feed along the feed delivery tray 164 over the culture trays 162, the feed passes through downwardly-facing holes 172 in the feed delivery tray 164 and is deposited on the feed collection trays 168, as is depicted in FIG. 12B. Because of the physical properties of the feed, feed will flow through the holes 172 until the feed ultimately backs up in the holes, resulting in a finite amount of feed being deposited into the feed collection tray 168. After the drag auger has dragged the feed past all of the holes 172, the actuator 146 can be actuated to dump the feed from one or more of the feed trays 168 and into one or more of the culture trays 162, as depicted in FIG. 12C. In some embodiments, each feed collection tray 168 can be individually controlled so that feed can be dumped into individual culture trays 162 as desired. Through individual control over the feed collection trays 168, the feed delivery system 160 can also be used selectively to supply feed to one or more individual trays 132 that are selected to receive feed.

Figure 13:
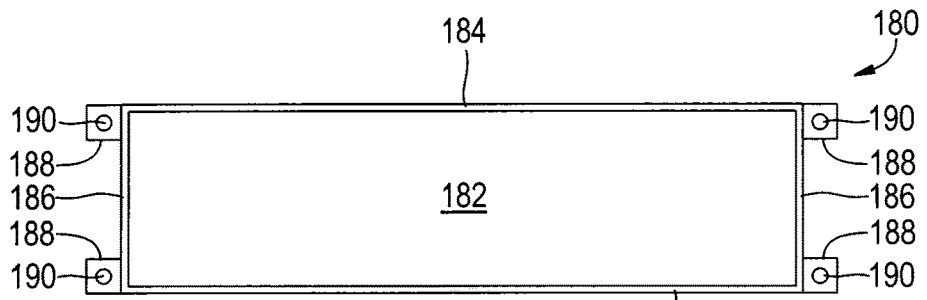
FIG. 13 is a top view of a first embodiment of a continuous culture tray.
Figure 14:
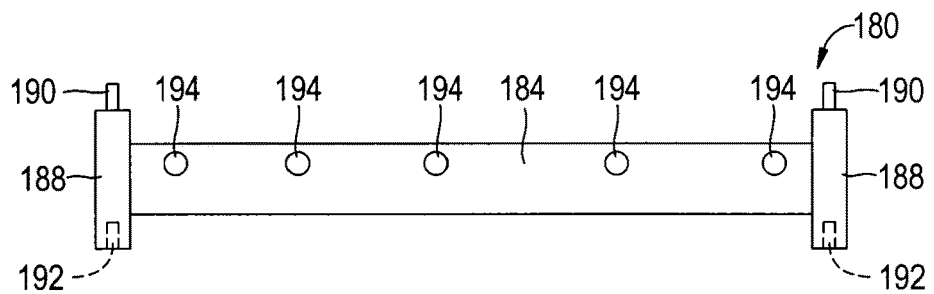
FIG. 14 is a side view of the culture tray of FIG. 13.
Figure 15:
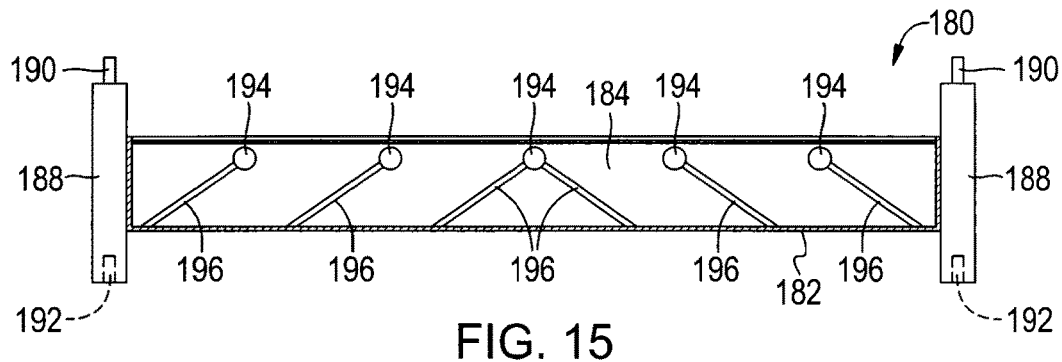
FIG. 15 is a cross-sectional view of the culture tray of FIG. 13.

FIGS. 13-16 illustrate a first embodiment for a culture tray 180 that can be used in continuous culture system, such as system 10 shown in FIGS. 1 and 2. Beginning with FIG. 13, the tray 180 comprises a generally planar floor 182, end walls 184, and side walls 186. By way of example, the tray 180 can be approximately 2 to 6 feet wide and 8 to 14 feet long. Attached to the exterior of the tray 180 are legs 188. More particularly, four legs 188 are provided on the tray 180, one positioned at each corner of the tray. As is shown in FIGS. 13-15, pegs 190 extend upwardly from the tops of the legs 188. The pegs 190 are adapted to be received by holes provided in the bottom of the legs of another tray 180. Similar holes 192 are shown in FIGS. 14 and 15. The pegs 190 serve to align the trays 180 when they are stacked and to provide structural stability to the stack.

As is apparent from the side view of FIGS. 14 and 15, holes 194 are formed in the side walls 184 adjacent the top edges of the walls. These holes 194 act as exits for mature larvae to migrate out of the tray 180. Because such migration facilitates collection of the larvae, the migration is also referred to as self-harvesting. To assist mature larvae in reaching the holes 194, ramps 196 are provided that extend up from the tray floor 182 to the holes. In particular, one ramp 196 is provided for each hole 194. As is shown most clearly in the cut-away view of FIG. 16, each ramp 196 can comprise a narrow, inclined, planar member that is attached along its entire length to the wall 184. In some embodiments, the ramps 196 do not form an angle larger than approximately 40 degrees with the floor 182 to make it easier for the mature larvae to escape. In further embodiments, the top surfaces of the ramps are provided with a high friction material to further facilitate self-harvesting.

Figure 16:
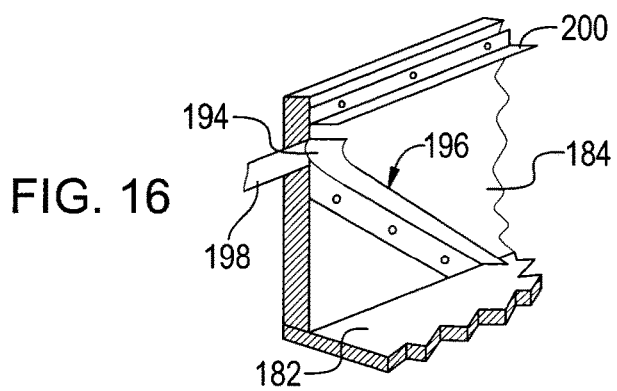
FIG. 16 is a cut-away perspective view of a portion of the culture tray of FIG. 13.

With further reference to FIG. 16, extending from the holes 194 are exit pipes 198 that deliver the exiting larvae to the aforementioned gutters (e.g., gutters 34 in FIG. 1) under the force of gravity. As is further illustrated in FIG. 16, the tray 180 can include a projecting lip 200 that prevents larvae from escaping the tray in any way other than through the holes 194.

Figure 17:
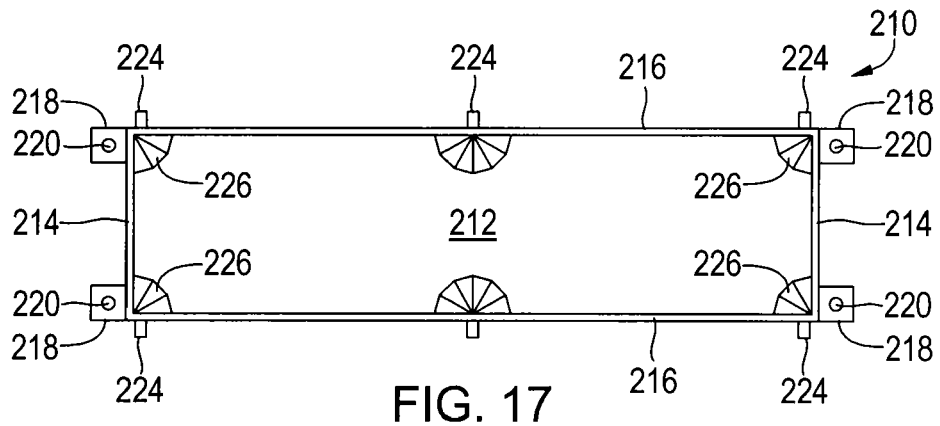
FIG. 17 is a top view of a second embodiment of a continuous culture tray.
Figure 18:
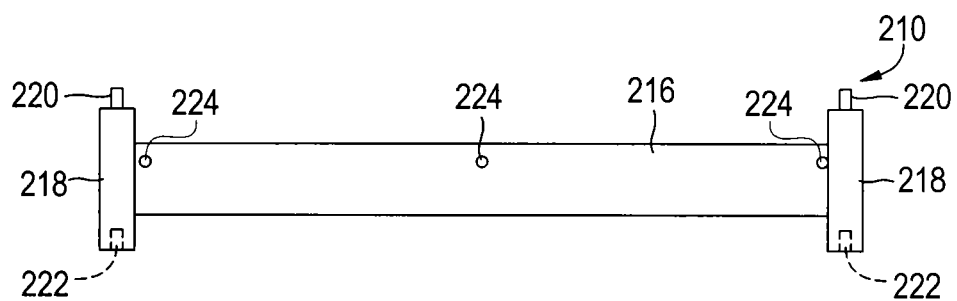
FIG. 18 is a side view of the culture tray of FIG. 17.
Figure 19:
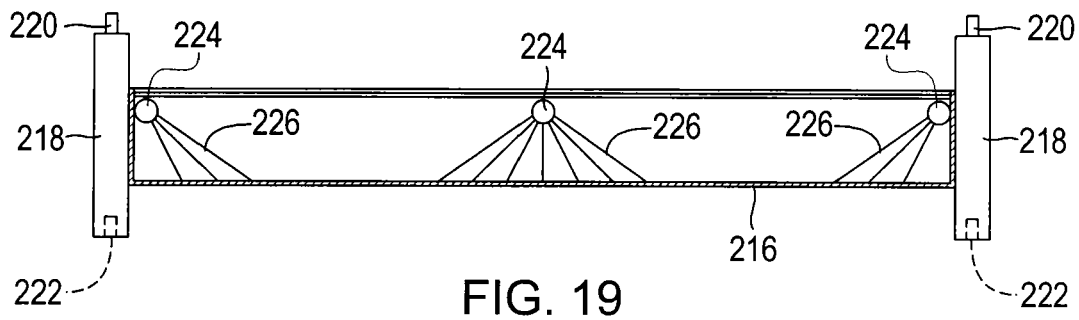
FIG. 19 is a cross-sectional view of the culture tray of FIG. 17.

FIGS. 17-20 illustrate a second embodiment for a culture tray 210 that can be used in continuous culture system, such as system 10 shown in FIGS. 1 and 2. Beginning with FIG. 17, the tray 210 comprises a generally planar floor 212, end walls 214, and side walls 216. Attached to the exterior of the tray 210 are legs 218. More particularly, four legs 218 are provided on the tray 210, one positioned at each corner of the tray. As is shown in FIGS. 17-19, pegs 220 extend upwardly from the tops of the legs 218. The pegs 220 are adapted to be received by holes provided in the bottom of the legs of another tray 210. Similar holes 222 are shown in FIGS. 18 and 19. The pegs 220 serve to align the trays 210 when they are stacked and to provide structural stability to the stack.

As is apparent from the side view of FIGS. 18 and 19, holes 224 are formed in the side walls 214 adjacent the top edges of the walls. These holes 224 act as exits for mature larvae to migrate out of the tray 210 and therefore are also self-harvesting holes. To assist mature larvae in reaching the holes 224, ramps 226 are provided that extend up from the tray floor 212 to the holes. In particular, one ramp 226 is provided for each hole 224. As is shown most clearly in the cut-away view of FIG. 20, each ramp 226 can be formed as a partial pyramid or cone. Therefore, the ramps 226 provide a wider entrance to the ramp. In some embodiments, the ramps 226 do not form an angle larger than approximately 40 degrees with the floor 212 and the top surfaces of the ramps are provided with a high friction material.

Figure 20:
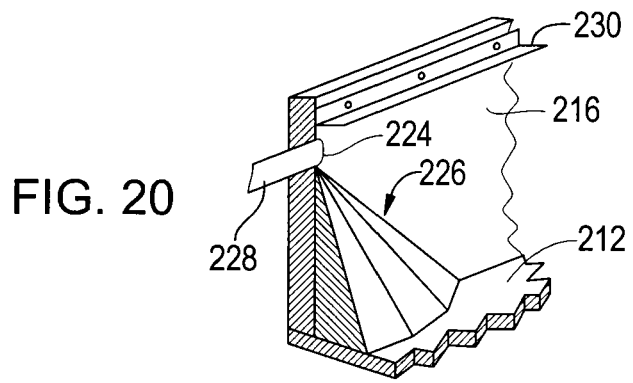
FIG. 20 is a cut-away perspective view of a portion of the culture tray of FIG. 17.

With further reference to FIG. 20, extending from the holes 224 are exit pipes 228 that deliver the exiting larvae to the aforementioned gutters (e.g., gutters 34 in FIG. 1). As is further illustrated in FIG. 20, the tray 210 can include a projecting lip 230 that prevents larvae from escaping the tray in any way other than through the holes 224.

Figure 21:
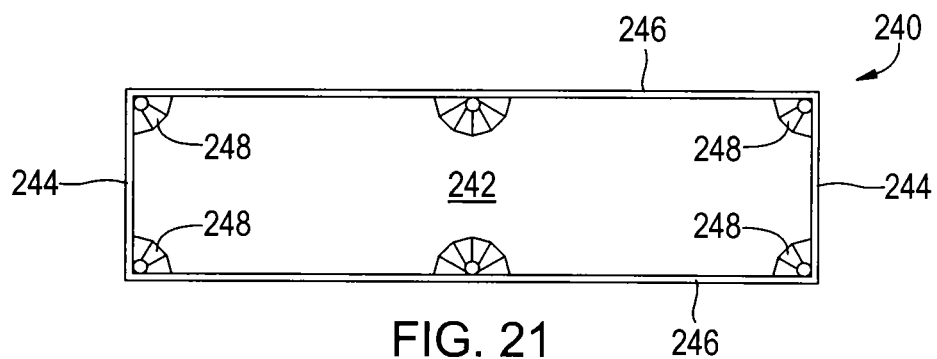
FIG. 21 is a top view of a third embodiment of a continuous culture tray.
Figure 22:
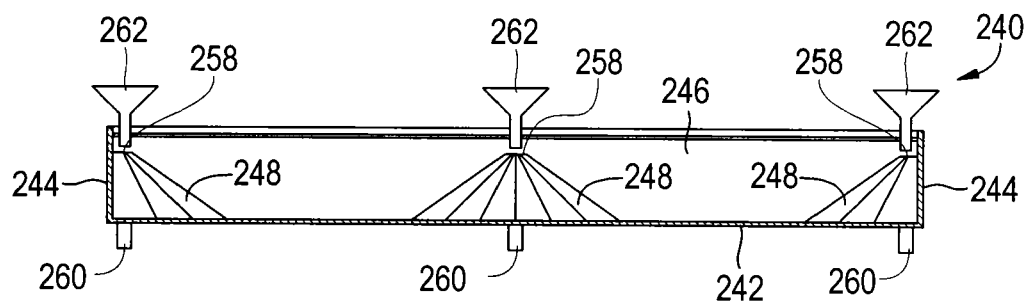
FIG. 22 is a cross-sectional view of the culture tray of FIG. 21.
Figure 23:
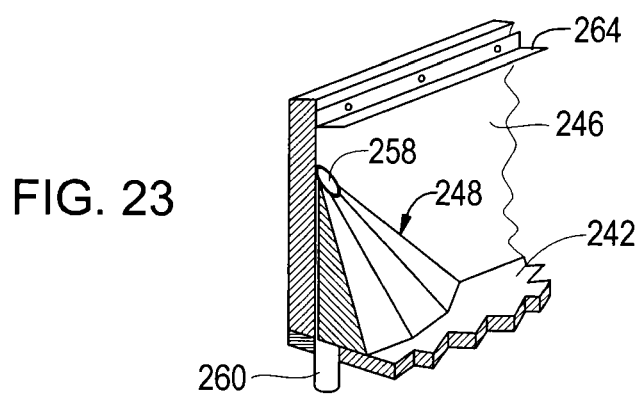
FIG. 23 is a cut-away perspective view of a portion of the culture tray of FIG. 21.

FIGS. 21-23 illustrate a third embodiment for a culture tray 240 that can be used in continuous culture system, such as system 10 shown in FIGS. 1 and 2. Beginning with FIG.

21, the tray 240 comprises a generally planar floor 242, end walls 244, and side walls 246. Although not depicted in FIGS. 21-23, the tray 240 can include legs similar to the legs described above in relation to FIGS. 13-20.

As is shown in the figures, ramps 248 are provided that extend up from the tray floor 242. Each ramp 256 can be formed as a partial pyramid or cone. In some embodiments, the ramps 256 do not form an angle larger than approximately 45 degrees with the floor 242 and the top surfaces of the ramps are provided with a high friction material. Formed through the top of each ramp 256 is a hole 258 into and through which mature larvae can fall. The holes 258 lead to vertical exit tubes 260, that in turn lead to a collection gutter.

As is shown in FIG. 22, associated with each ramp 248 and hole 258 is a funnel 262. The funnels 262 are used to catch and pass on larvae that have exited trays above the tray 240. Therefore, mature larvae that exit their trays 240 fall through the funnels 262 and the exit tubes 260 until finally reaching the gutter. As is further illustrated in FIG. 23, the tray 240 can include a projecting lip 264 that prevents larvae from escaping the tray in any way other than through the holes 258.

Example continuous culture systems and trays having been described above, the larvae rearing process will now be described. As described above, many existing larvae rearing systems are batch systems in which larvae and larval feed are placed into a large receptacle. The larvae eat the feed over the course of several days or weeks and are then manually harvested by removing the contents of the receptacle and separating the mature larvae from the remainder of the contents (e.g., uneaten feed and residue). This process is inefficient both because it is labor intensive and because much of the feed may rot before it is consumed.

With a continuous culture system such as the system 10 shown in FIGS. 1 and 2, which can use culture trays such as those shown in FIGS. 13-23, manual harvesting is not performed and clearing of the trays does not need to be performed as frequently. In an example larvae rearing process, insect eggs or small larvae (which have been reared separately) are deposited in the culture trays and larval feed is automatically delivered to the culture trays using the feed delivery system, for example, one of the feed delivery systems shown in FIGS. 5-12. In some embodiments, just enough feed is provided by the feed delivery system each day to match the amount of feed that the larvae will consume in a day. This way, rotting of the feed is avoided. In addition, water is provided to the trays as necessary by the water delivery system to maintain the desired level of moisture in the trays.

Over time, the larvae grow and mature. This maturation may take approximately 10-20 days, depending upon the particular larvae and the feed rate, as well as the conditions, such as temperature and humidity. In some embodiments, the temperature of the room in which the trays are located is maintained at a temperature of approximately 80° F. to 100° F. and a relative humidity of approximately 40% to 80%. Once the larvae have matured to their prepupae state, they can no longer eat the feed that is provided in the trays and their natural instinct is to migrate away from the larvae to find a place to pupate. It is this migration that causes the larvae to move to the exits of the trays and self-harvest. In some embodiments, the larvae can be encouraged to migrate by misting the trays because, in nature, prepupae prefer to migrate on rainy days. As the larvae leave the trays, they slide down the exit pipes and are collected in the gutters from which they can be either manually collected or driven by conveyors to a processing location. Prepupae can also be stimulated to migrate using a vibrator that activated for short periods of time, for example once each hour. Such a vibrator can be attached near the center of a tray stack and can be of such power that the entire stack is vibrated. The vibrations created by the vibrator cause the prepupae to seek a more quiet location. In the above-described process, eggs or young larvae can be periodically added to the trays. Therefore, the process is a continuous one in which young larvae are added to the trays and mature larvae exit the trays. Over time, residue from the feed, such as the fibrous components of the feed and larval waste, will collect. Once this residue nears the exits of the trays (e.g., after many weeks or several months), the residue can be removed. In some embodiments, removal can be achieved by vacuuming out the contents of the trays. Regardless of the manner in which the contents of the trays are removed, however, the trays can be used to rear many generations of larvae in between such removal.

Figure 24:
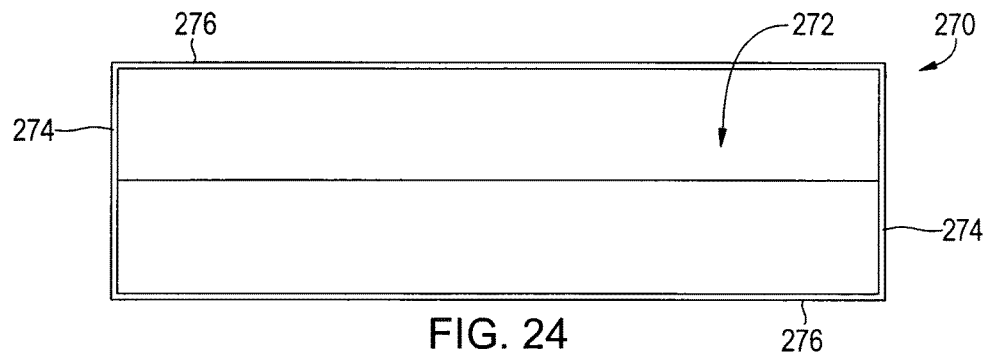
FIG. 24 is a top view of a first embodiment of a batch culture tray.
Figure 25:
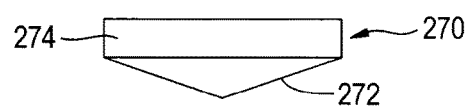
FIG. 25 is an end view of the culture tray of FIG. 24

FIGS. 24 and 25 illustrate a first embodiment for a culture tray 270 that can be used in a batch culture system, such as system 40 shown in FIGS. 3 and 4. Beginning with FIG. 24, the tray 270 comprises a floor 272, end walls 274, and side walls 276. By way of example, the tray 270 can be approximately 2 to 6 feet wide and 8 to 14 feet long. As is shown in FIG. 25, the floor 272 can be sloped so as to have a generally V-shaped cross-section. By way of example, two lateral portions of the floor 272 slope toward the middle of the tray 270 at an angle of approximately 3 to 15 degrees. With such a tray 270, the contents of the tray can be manually removed after each batch of larvae have matured, for example using a vacuum hose. Practical tests have shown that culture trays can be emptied very quickly with a large vacuum device.

Figure 26:
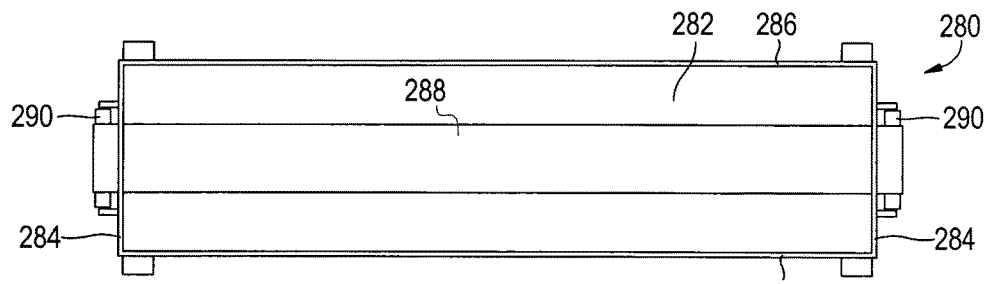
FIG. 26 is a top view of a second embodiment of a batch culture tray.
Figure 27:
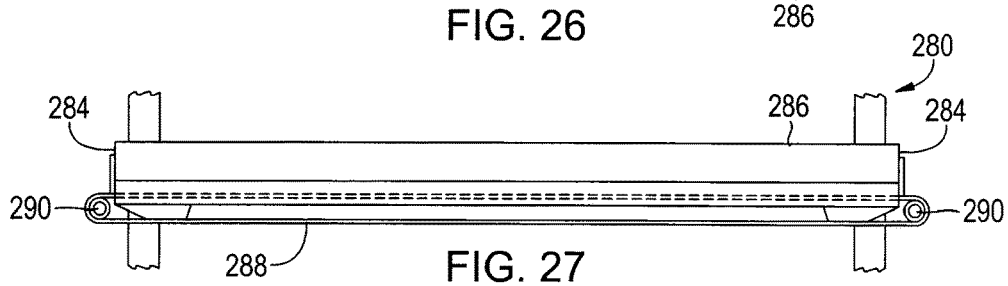
FIG. 27 is a side view of the culture tray of FIG. 26.
Figure 28:
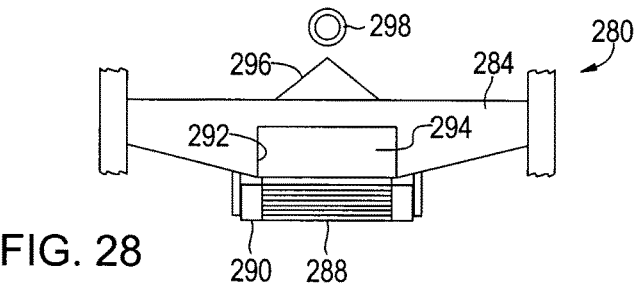
FIG. 28 is an end view of the culture tray of FIG. 26.

FIGS. 26-28 illustrate a second embodiment for a culture tray 280 that can be used in a batch culture system, such as system 40 shown in FIGS. 3 and 4. Beginning with FIG. 26, the tray 280 comprises a floor 282, end walls 284, and side walls 286. As is shown in FIG. 25, the floor 282 can also be sloped so as to have a generally V-shaped cross-section. As is shown in FIGS. 26 and 27, however, the tray 280 further includes a conveyor having an endless conveyor belt 288 that loops from underneath the tray and into the tray to form a "live" bottom of the tray. The conveyor belt 288 can be mounted on rollers 290 at each end of the tray 280, at least one of which can be selectively driven. In addition, as is shown in FIG. 28, at least one of the end walls 284 includes an exit comprising an opening 292 and a door 294. As is also shown in FIG. 28, a sloped feed splitter 296 having a triangular cross-section can optionally be used to spread feed along the bottom of the tray 280 that is delivered to the tray using a feed line 298.

At maturity, larvae within the tray 280 can be automatically harvested by opening the door 294 and driving the conveyor belt 288. The contents of the tray 280 can be collected using an appropriate receptacle (e.g., hopper connected to a further conveyor), and the larvae can be separated from the remainder of the material from the tray in another location.

Figure 29:
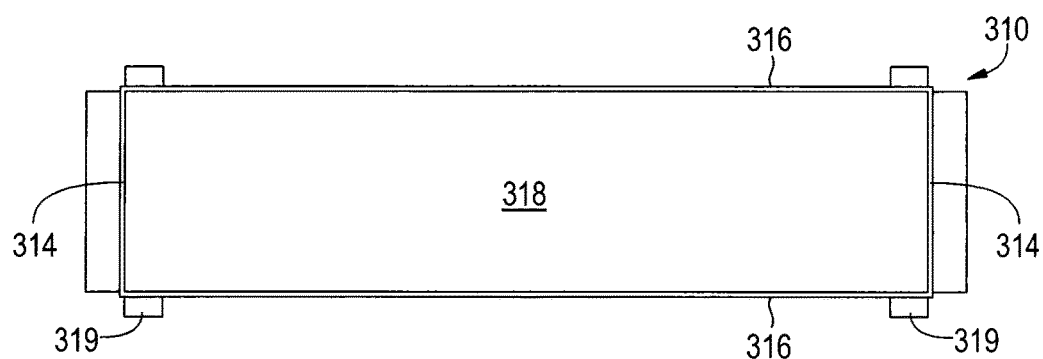
FIG. 29 is a top view of a third embodiment of a batch culture tray.
Figure 30:
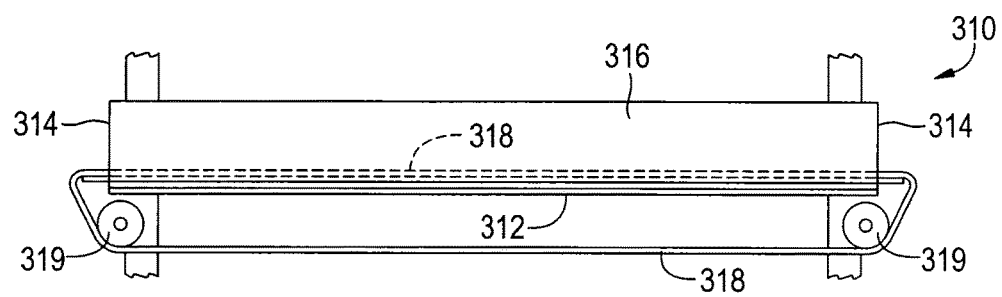
FIG. 30 is a side view of the culture tray of FIG. 29.
Figure 31:
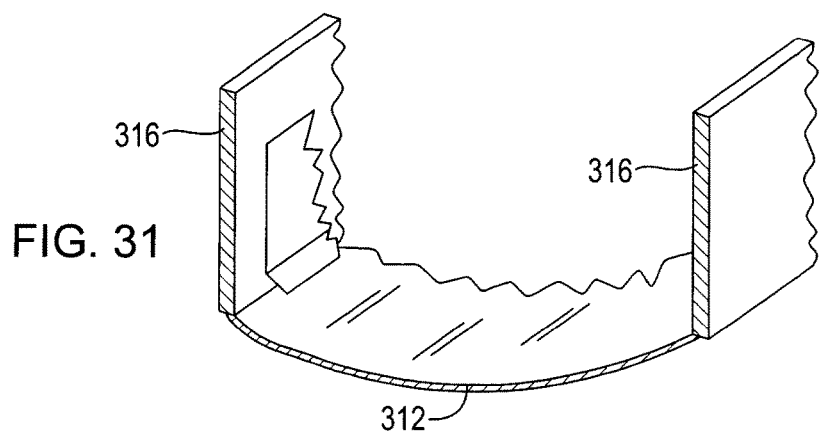
FIG. 31 is a cut-away perspective view of a portion of the culture tray of FIG. 29.

FIGS. 29-31 illustrate a third embodiment for a culture tray 310 that can be used in a batch culture system, such as system 40 shown in FIGS. 3 and 4. The tray 310 comprises a floor 312, end walls 314, and side walls 316. As is shown in FIG. 31, the floor 312 can be convex in cross-section so as to bow downwardly along the central longitudinal axis of the tray 310. As is shown best in FIG. 30, the tray 310 also includes a conveyor having an endless conveyor belt 318 that loops from underneath the tray and into the tray to form a live bottom of the tray. The conveyor belt 318 can be mounted on rollers 319 at each end of the tray 310, at least one of which can be selectively driven. In some embodiments, at least one of the end walls 284 includes an exit comprising an opening and a door in similar manner to that shown in FIG. 28.

When they are mature, larvae grown in the tray 310 can be automatically harvested by opening the door and driving the conveyor belt 318. The contents of the tray 310 can be collected using an appropriate receptacle (e.g., hopper connected to a further conveyor), and the larvae can be separated from the remainder of the material from the tray in another location.

Figure 32:
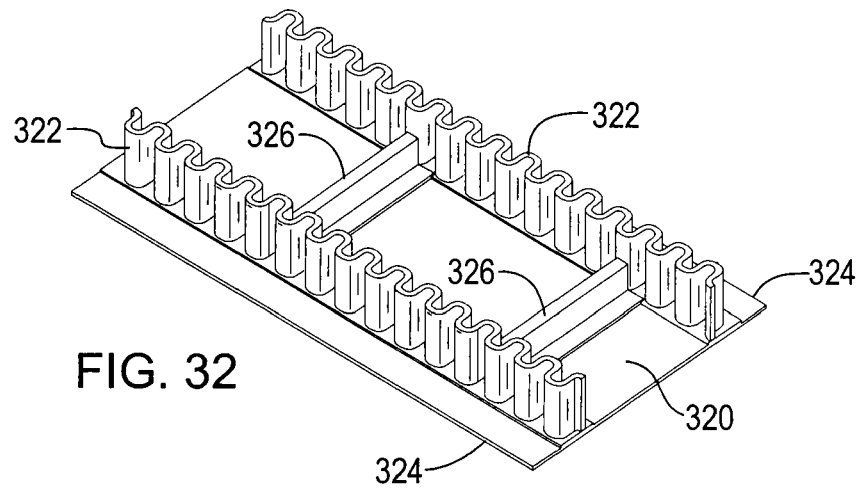
FIG. 32 is a perspective view of an alternative conveyor belt arrangement for a larvae rearing system.
Figure 33:
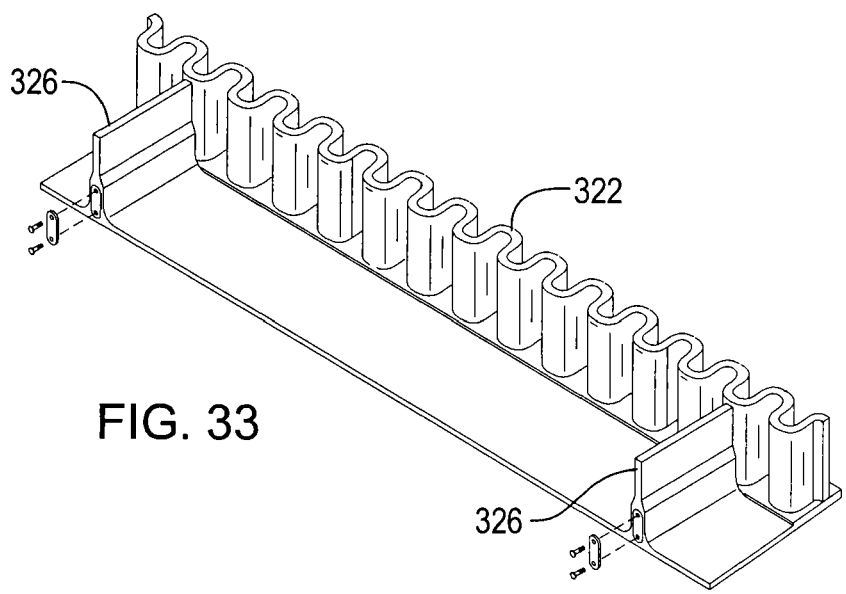
FIG. 33 is a cut-away perspective view of a portion of the arrangement of FIG. 32.

FIGS. 32 and 33 illustrate an alternative conveyor belt arrangement in which the belt forms a tray in which larvae are reared. As is shown in FIG. 32, the arrangement comprises a flat bottom conveyor belt 320 having integrated corrugated sides 322 that, for example, are approximately 6 to 10 inches tall. Provided along the length of the conveyor belt 320 are periodically spaced vertical dividers 326 that extend transversely across the belt to its sides 322. The arrangement shown in FIGS. 32 and 33 is useful in situations in which it is desirable to move all of the material and larvae in a line to one end of a building where they will be dumped into a separating or transport system. Such functionality eliminates the need for gutter or vacuum systems and enables the aisles between the rows of culture trays to be more narrow and therefore achieves a higher tray density within a given floor area.

In the above disclosure, many different embodiments were described for many different components. It is noted that several other embodiments are possible. While certain components have been described as suitable for use in particular systems, it is further noted that those components can be used in other systems. For instance, while the continuous culture trays have been described as suitable for use in the stackable system of FIGS. 1 and 2, the trays could alternatively be used in a cantilevered system, such as that of FIGS. 3 and 4. Similarly, while batch culture trays have been described as suitable for use in the cantilevered system of FIGS. 3 and 4, the trays could alternatively be used in a stackable system, such as that of FIGS. 1 and 2.

The invention claimed is:

1. A system for rearing larvae, the system comprising:
a plurality of culture trays arranged in at least one stack of trays, each stack comprising multiple levels of trays, each tray comprising an open-topped basin adapted to receive larvae and larval food;
a feed delivery system adapted to automatically deliver larval feed to individually selected culture trays, the feed delivery system comprising multiple feed lines, one feed line provided above each level of culture trays of the at least one stack; and
a water delivery system adapted to automatically deliver water to the culture trays.

2. The larvae rearing system of claim 1, wherein the culture trays are arranged in elongated rows.

3. The larvae rearing system of claim 1, wherein the culture trays comprise legs that are adapted to couple with legs of at least one other culture tray in a stack of trays.

4. The larvae rearing system of claim 1, wherein at least one culture tray comprises an opening through which mature larvae can exit the tray.

5. The larvae rearing system of claim 4, wherein the opening is positioned near a top edge of the at least one culture tray.

6. The larvae rearing system of claim 4, wherein the at least one culture tray further comprises a ramp that leads to the opening along which the mature larvae can crawl to reach the opening.

7. The larvae rearing system of claim 6, wherein the ramp is configured as a narrow, planar member that is attached along its length to a side wall of the at least one culture tray.

8. The larvae rearing system of claim 6, wherein the ramp is configured as a partial pyramid or partial cone.

9. The larvae rearing system of claim 8, wherein the opening is integrated into the ramp and the at least one culture tray includes an exit tube through which the mature larvae can pass, the opening leading to the exit tube.

10. The larvae rearing system of claim 9, further comprising a funnel positioned above the opening and the exit tube that is adapted to receive mature larvae that have exited a culture tray positioned above the at least one culture tray.

11. The larvae rearing system of claim 4, wherein the at least one culture tray comprises an exit tube associated with the opening through which the mature larvae can pass.

12. The larvae rearing system of claim 11, further comprising a gutter into which the mature larvae can fall after passing through the exit tube.

13. The larvae rearing system of claim 1, wherein the culture trays are supported by a frame that comprises support posts from which laterally extend support platforms on which the culture trays are supported.

14. The larvae rearing system of claim 1, wherein at least one culture tray comprises a sloped floor having a generally V-shaped cross-section.

15. The larvae rearing system of claim 1, wherein at least one culture tray comprises an integrated conveyor having a conveyor belt that forms a live bottom of the tray, the conveyor belt being configured to convey material from within the tray to another location.

16. The larvae rearing system of claim 15, wherein the at least one culture tray comprises a wall at an end of the conveyor having a door that can be opened when the conveyor is operated to enable the material to be conveyed out from the tray.

17. The larvae rearing system of claim 15, wherein the conveyor belt covers a central portion of a floor of the at least one culture tray.

18. The larvae rearing system of claim 15, wherein the conveyor belt covers substantially the entirety of a floor of the at least one culture tray.

19. The larvae rearing system of claim 1, wherein the feed lines each comprise a feed tube through which feed can travel.

20. The larvae rearing system of claim 19, wherein the feed delivery system further comprises hoppers and flexible, hollow augers that extend from the hoppers and through the feed tubes, the feed delivery system further comprising motors that rotate the augers within the feed tubes to transport feed from the hoppers along the feed tubes.

21. The larvae rearing system of claim 20, wherein the feed delivery system further comprises rotatable sleeves that are provided over the feed tubes, one sleeve been provided for each culture tray, the sleeves having holes that can be aligned with openings in the feed tubes by selectively rotating the sleeves relative to the feed tubes to enable feed to pass from the feed tubes to selected culture trays.

22. The larvae rearing system of claim 19, wherein the feed delivery system further comprises hoppers and pistons that are used to drive feed through the feed tubes.

23. The larvae rearing system of claim 22, wherein the pistons are hollow pistons and wherein the feed delivery system further comprises at least one check valve that prevents backflow of the feed.

24. The larvae rearing system of claim 1, wherein the feed lines each comprise a feed delivery tray and a flexible, hollow auger that is provided within the feed delivery tray.

25. The larvae rearing system of claim 24, further comprising a motor that is adapted to drag the auger along the feed delivery tray and wherein the feed delivery tray has downwardly-facing openings positioned above each culture tray in the level of culture trays.

26. The larvae rearing system of claim 25, wherein the feed delivery system further comprises a slidable sleeve mounted to the underside of the feed delivery tray above each culture tray in the level, each sleeve having holes that can be aligned with the openings in the feed delivery tray by selectively laterally displacing the sleeve relative to the feed delivery tray so as to enable feed to pass from the feed delivery tray to selected culture trays.

27. The larvae rearing system of claim 25, wherein the feed delivery system further comprises a rotatable feed collection tray positioned underneath the feed delivery tray and above each culture tray in the level, wherein feed that drops through the openings in the feed delivery tray onto the feed collection trays can be dropped into selected culture trays by selectively rotating the feed collection trays.

28. A feed delivery system for use in a larvae rearing system that comprises a plurality of culture trays arranged in at least one stack of trays having multiple levels of trays, each tray comprising an open-topped basin adapted to receive larvae and larval food, the feed delivery system comprising:
   multiple feed lines, one feed line positioned above each level of culture trays such that each feed line is adapted to deliver feed to multiple trays; and
   feed drive means for driving feed along the feed lines, wherein the feed drive means comprise flexible, hollow augers that extend through the feed tubes and motors that rotate the augers within their feed tubes.

29. The feed delivery system of claim 28, wherein the feed lines each comprise a feed tube that is positioned above each level of culture trays.

30. The feed delivery system of claim 28, further comprising rotatable sleeves that are provided over the feed tubes, one sleeve been provided for each culture tray, the sleeves having holes that can be aligned with openings in the feed tubes by selectively rotating the sleeves relative to the feed tubes to enable feed to pass from the feed tubes to selected culture trays.

\* \* \* \* \*